United States Patent
Jann et al.

(10) Patent No.: US 6,312,733 B1
(45) Date of Patent: Nov. 6, 2001

(54) **ICE CRYSTAL GROWTH INHIBITING AGENTS FROM *ZOARCES VIVIPARUS***

(75) Inventors: Alfred Jann, Publier (FR); Rolv Lundheim, Trondheim (NO)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/117,588

(22) PCT Filed: Feb. 5, 1997

(86) PCT No.: PCT/EP97/00547

§ 371 Date: Mar. 8, 2000

§ 102(e) Date: Mar. 8, 2000

(87) PCT Pub. No.: WO97/28698

PCT Pub. Date: Aug. 14, 1997

(30) Foreign Application Priority Data

Feb. 9, 1996 (EP) .................................................. 96200309

(51) Int. Cl.[7] .............................. A61K 35/16; A23J 3/12
(52) U.S. Cl. ......................... 424/531; 426/657; 530/350
(58) Field of Search ......................... 424/531; 426/657; 530/350

(56) References Cited

U.S. PATENT DOCUMENTS 5,869,092 * 2/1999 Hays et al. .

FOREIGN PATENT DOCUMENTS

WO 92 12722A 8/1992 (WO) .

OTHER PUBLICATIONS

Greenwood et al., "Effect of chronic irradiation on th humoral immune response of a marine fish, the eelpout, *Zoarces vivparus*", Internat. J. Rad. Biol. 67 (1): 71–77 (1995).*

Korsgaard, "Calcium Metabolism in Relation to Ovarian Functions During Early and Late pregnancy in the vivparous blenny, *Zoarces viviparus*", J. Fish Biol. 44 (4): 661–672 (1994).*

Cheng et al., "Structures of Antifreeze Peptides from the Antarctic Eel Pout, Austrolycicthys brachycephaulus", BBA 997: 55–64 (Jan. 1989).*

Schrag et al., "Primary and Secondary Structur of Antifreeze Peptides from Arctic and Antarctic Zoarcid Fishes", BBA 915: 357–70 (May 1987).*

Swientek, R.J., "Frozen foods with 'fresh' qualities; Antifreeze polypeptides and proteins inhibit ice crystal formation"; Food Processing, p. 55, (October 1992).

Knight, C.A., et al., "Adsorption of α– helical antifreeze peptides on specific ice crystal surface planes", Biophysical Journal, vol. 59, pp. 409–418, (Feb. 1991).

Knight, C.A., et al., "Solute Effects on Ice Recrystallization: An Assessement Technique"; Cryobiology, vol. 25, pp. 55–60, (1988).

Davies, P.L., et al., "Biochemistry of fish antifreeze proteins", The FASEB Journal, vol. 4, pp. 2460–2468, (May 1990).

Food Technology, vol. 47, No. 1, Jan. 1, 1993, pp. 82, 84–88, 90, Feeney et al. "Antifreeze proteins: Properties, Mechanism of Action, and Possible Applications".

Polar Biology, vol. 1, No. 2, 1982, pp. 115–123, T. Schneppenheim, "Freezing–Point Depressing Peptides and Glycoproteins from Artic–Boreal and Antarctic Fish".

Canadian Journal of Zoology, vol. 66, No. 2, 1988, pp. 2611–2617, Davies, Hew Fletcher, "fish antifreeze proteins: physiology and evolutionary biology".

* cited by examiner

Primary Examiner—Sandra E. Saucier
(74) Attorney, Agent, or Firm—Winston & Strawn

(57) ABSTRACT

Ice crystal growth inhibiting agents and process for preparing an extract of these agents in which Zoarces viviparus blood is extracted, it is cooled, the supernatant constituting the *Zoarces viviparus* serum containing the ice crystal growth inhibiting agents is collected, and then the supernatant is frozen. The present invention also relates to a process for using these agents for the manufacture of a food product.

20 Claims, No Drawings

ICE CRYSTAL GROWTH INHIBITING AGENTS FROM ZOARCES VIVIPARUS

FIELD OF THE INVENTION

The subject of the present invention is ice crystal growth inhibiting agents, a process for preparing such agents and a process for using these agents in the manufacture of a food product.

BACKGROUND OF ART

It is known that ice crystal growth inhibiting agents called "thermal hysteresis proteins" have the capacity to bind to ice crystals and to reduce their growth (Biophysical Journal, February 1991, p 409–418). Two properties of these agents have been demonstrated: they have the capacity to reduce the apparent freezing temperature of a solution without affecting its thawing temperature and they also have the capacity to inhibit the recrystallization of ice crystals (Cryobiology, vol. 25, 1988, p 55–60).

Furthermore, three types of ice crystal growth inhibiting agents have been demonstrated in certain Arctic and Antarctic fish in particular (The FASEB Journal, May 1990, p 2460–2468). These agents are of a protein structure or of a glycoprotein structure. They were isolated from the plasma or the serum of these fish and then purified. However, they are also present in other tissues.

It is also known to use ice crystal growth inhibiting agents to improve the quality of food products such as frozen desserts, frozen pastes or fresh products, such as tomatoes. DNA Plant Technology Corp has synthesized an artificial protein which is an ice crystal growth inhibiting agent similar to those which can be found in certain fish or other organisms capable of living under very low temperature conditions (Food Processing, October 1992, p 55).

However, up until now, no ice crystal growth inhibiting agent has been isolated in Zoarces viviparus, a fish living in particular on the coasts of Norway and on the coasts of the Baltic Sea.

SUMMARY OF THE INVENTION

The aim of the present invention is to provide new ice crystal growth inhibiting agents having a remarkable level of activity and capable of being advantageously used in particular in the freezing or texturing of products such as food products for example.

To this effect, the ice crystal growth inhibiting agents according to the present invention are agents extracted from Zoarces viviparus having a molecular weight of 4–5.5 kDa, capable of being obtained by a process in which Zoarces viviparus serum is collected, the serum proteins are isolated, the proteins are separated by gel filtration and the protein fraction having a thermal hysteresis of 1–1.8° C. is isolated.

Preferably, these ice crystal growth inhibiting agents exhibit a thermal hysteresis of 1.3–1.5° C.

It has been observed, surprisingly, that these ice crystal growth inhibiting agents effectively make it possible to reduce the size of the ice crystals during the freezing of food products such as ice creams, frozen desserts or frozen pastes for example and thus confer a more unctuous texture on the latter.

DETAILED DESCRIPTION OF THE INVENTION

In the remainder of the description, the expression "crystal inhibiting agent" will be used in the sense of "ice crystal growth inhibiting agent".

In the remainder of the description, the expression "typical size of the crystals" will be used in the sense of "size of the ice crystals which is predominantly found".

In the remainder of the description, the expression "equivalent diameter" will be used in the sense of "diameter of a circle which has the same surface area as the image of the crystal considered".

In the process for preparing an extract of ice crystal growth inhibiting agents according to the present invention, Zoarces viviparus serum containing the said agents is prepared.

To do this, Zoarces viviparus blood may be extracted, it may be cooled, the supernatant constituting the Zoarces viviparus serum containing the ice crystal growth inhibiting agents may be collected and then the supernatant may be frozen, for example.

The Zoarces viviparus blood may be extracted with the aid of a treated capillary, in particular a capillary treated with sodium heparin, for example.

The Zoarces viviparus blood may be cooled to 0–5° C. so as to, in particular, inhibit the activity of the proteases and peptidases contained in the blood, for example.

The supernatant constituting the Zoarces viviparus serum containing the ice crystal growth inhibiting agents may be collected by centrifuging Zoarces viviparus blood at 1000–5000 g at 0–5° C. for 5–15 min, for example. To do this, a Heraeus Minifuge GL type centrifuge, marketed by Heraeus SA, 23, route des Jeunes, CH-1227 Carouge-Geneva, may be used for example.

The supernatant may be frozen at a temperature of between −15° C. and −40° C., for example.

The present invention also relates to a process for reducing the size of ice crystals, in which at least one ice crystal growth inhibiting agent extracted from Zoarces viviparus is added to a food product. It is possible in particular to add 0.01–10% of ice crystal growth inhibiting agents according to the present invention to a food product during its preparation.

The food product thus prepared may then be frozen for example. It may in particular be frozen at a temperature of between −15° C. and −40° C.

EXAMPLES

The crystal growth inhibiting agents according to the present invention are described in greater detail with the aid of the biochemical data and through the various properties determined in particular with the aid of various tests below. The percentages are given by weight, unless otherwise stated.

Demonstration of the Crystallization of Ice Crystals from a 20% Sucrose Solution in the Presence of Zoarces viviparus Serum.

6 samples of 1 ml of a 20% sucrose solution are prepared to which Zoarces viviparus serum, containing crystal inhibiting agents, is added at various concentrations.

The samples are kept in the refrigerator before being placed under a Polyvar type microscope, marketed by Reichert-Jung, Harnalser Hauptstrasse 219, AT-1170 Vienna and being rapidly cooled down to a temperature of −100° C. with the aid of a Lincam type temperature controller marketed by Lincam Scientific Instruments LTD, Epsom Downs Metro Centre, Waterfield, Tadworth, Surrey, KT20 5HT-UK.

Next, the samples are heated to a temperature of −9° C. and the size of the crystals contained in the samples thus prepared is observed under a Polyvar type microscope within a time interval of 30 to 120 min In parallel, a control sample containing 1 ml of a 20% sucrose solution is prepared under the same conditions.

The % of *Zoarces viviparus* serum containing the crystal inhibiting agents which are added to the samples of a 20% sucrose solution are given in volume.

Sample 1: 1.3% of *Zoarces viviparus* serum is added to 1 ml of a 20% sucrose solution and then the sample is prepared as indicated above. After 60 min at −9° C., the crystals have a typical size of less than 2 $\mu$m. No variation is observed in the size of the crystals over time.

Sample 2: 1% of *Zoarces viviparus* serum is added to 1 ml of a 20% sucrose solution and then the sample is prepared as indicated above. After 30 min at −9° C., the crystals have a typical size of less than 2 $\mu$m. No variation is observed in the size of the crystals over time.

Sample 3: 0.1% of *Zoarces viviparus* serum is added to 1 ml of a 20% sucrose solution and then the sample is prepared as indicated above. After 30 min at −9° C., the crystals have a typical size of less than 15 $\mu$m. The size of the crystals varies only very slightly over time. After 120 min at −9° C., the typical size of the crystals remains less than 15 $\mu$m and the crystals have shapes with pronounced angles.

Sample 4: 0.02% of *Zoarces viviparus* serum is added to 1 ml of a 20% sucrose solution and then the sample is prepared as indicated above. The size of the crystals varies slightly between,60 min and 90 min at −9° C. The typical size of the crystals is less than 20 $\mu$m after 90 min at −9° C. The crystals have shapes with pronounced angles.

Sample 5: 0.013% of *Zoarces viviparus* serum is added to 1 ml of a 20% sucrose solution and then the sample is prepared as indicated above. The same variation is observed in the size of the crystals as for the sample prepared with 0.02% of *Zoarces viviparus* serum. The typical size of the crystals is greater than 20 $\mu$m after 90 min at −9° C. The crystals have shapes with slightly round angles.

Sample 6: 0.01% of *Zoarces viviparus* serum is added to 1 ml of a 20% sucrose solution and then the sample is prepared as indicated above. A greater variation is observed in the size of the crystals than for the sample prepared with 0.013% of *Zoarces viviparus* serum. Furthermore, the crystals have more rounded shapes than for the sample prepared with 0.013% of Zoarces viviparus serum. The typical size of the crystals is greater than 25 $\mu$m after 90 min at −9° C.

Control sample: A 20% sucrose solution is prepared as In indicated above but without adding *Zoarces viviparus* serum thereto. The crystals rapidly grow bigger. Their shape is round and after 90 min at −9° C., the typical size of the crystals is greater than 25 $\mu$m.

Thus, if *Zoarces viviparus* serum at a concentration of 1.3 to 0.013% is added to a 20% sucrose solution, relatively small ice crystals whose size varies only very slightly over time are observed under a microscope.

On the other hand, if a very low concentration of *Zoarces viviparus* serum is added to a 20% sucrose solution, the ice crystals grow bigger more rapidly.

Between sample 6 and the control sample is the limit where very few differences are observed in the shape and in the variation in the size of the ice crystals.

If the concentration of *Zoarces viviparus* serum contained in a 20% sucrose solution is between 0.01% and 10%, it is observed that the shapes of the crystals have more pronounced angles than those of the crystals of a control solution not containing the said serum.

Measurement of Thermal Hysteresis

This analysis is carried out with the aid of a Clifton Nanolitre Osmometer type temperature controller marketed by Clifton Technical Physics, P.O. Box, Hartford, U.S.—New York, 12830 and a Wild MZ8 type stereomicroscope marketed by Leica A. G., Verkaufsgesellschaft, Kanalstrasse 21, CH-8152 Glattbrugg.

To do this, a 20 ml fraction of a sample of *Zoarces viviparus* serum is collected at room temperature and it is deposited in a receptacle placed in the temperature controller. The said receptacle contains liquid paraffin. Rapid freezing is performed followed by gradual thawing; the thawing of the crystals is observed with the aid of a stereomicroscope. Next, this thawing is slowed down and stopped so as to stabilize the sole small-sized crystal remaining and the temperature is then noted. This temperature is the thawing point. Next, gentle cooling is performed and the temperature at which the crystal begins to grow in size is noted. This temperature is the apparent freezing point.

The thermal hysteresis value is then calculated by calculating the difference between the apparent freezing point and the thawing point. The thermal hysteresis value of the *Zoarces viviparus* serum fraction is 1.4° C., which corresponds to a high value for a fish containing such agents.

Characterization of the Ice Crystal Growth Inhibiting Agents Extracted from *Zoarces viviparus*

The ice crystal growth inhibiting agents extracted from *Zoarces viviparus* are characterized by chromatographic analysis followed by separation by polyacrylamide gel electrophoresis.

A chromatographic analysis is therefore first carried out. To do t his, the proteins of 20 mg contained in the *Zoarces viviparus* serum are separated on a superose 12 column marketed by Pharmacia Biotech A. G., Dübendorf, CH, with a Waters 519 pump and a DAD Waters 990 detector which are marketed by Waters A. G, Volketswil, CH. To carry out the separation by liquid chromatography, a 150 mM ammonium carbonate buffer pH 7.8 is used as mobile phase at a flow rate of 0.5 ml/min.

Using the fractions eluted by chromatography, measurement of thermal hysteresis is carried out as described in the test "measurement of thermal hysteresis". The fact that the fraction eluting between 30 and 33 minutes is that which contains the *Zoarces viviparus* ice crystal growth inhibiting agents is thus demonstrated since it is in this fraction that the maximum thermal hysteresis is measured.

This fraction which is active in thermal hysteresis is concentrated and then separated by gel electrophoresis. This separation is carried out at 100 V for 100 min on a pre-manufactured gel, Ready gels, marketed by BIO-RAD, Glattbrugg, CH, with a Mini Protean II apparatus marketed by BIO-RAD, Glattbrugg, CH.

After staining, the molecular weight of the proteins contained in this fraction is evaluated by comparison with a range of molecular weight standards of between 26.6 and 1.4 kDa, marketed by BIO-RAD, Glattbrugg, CH, separated on the same gel.

The fact that the proteins in the fraction which is active in thermal hysteresis have a molecular weight of 4–5.5 kDa is thus demonstrated.

Study of the Influence of Heat on the Activity of the Crystal Formation Inhibiting Agents Contained in the *Zoarces viviparus* Serum Samples of *Zoarces viviparus* serum are heated for 2 h at 40° C., at 50° C., at 60° C., at 70° C. and at 80° C. and then the thermal hysteresis of these samples is measured. The thermal hysteresis values of these various samples are compared with the thermal hysteresis value of a *Zoarces viviparus* serum sample kept at room temperature.

To do this, the procedure is carried out as described in the test "measurement of thermal hysteresis".

The thermal hysteresis values for these serum samples are stated in Table I below.

TABLE I

| Heat-treated sample | Thermal hysteresis value (° C.) |
|---|---|
| Control sample treated 2 h at 20° C. | 0.232 |
| Sample treated 2 h at 40° C. | 0.208 |
| Sample treated 2 h at 50° C. | 0.186 |
| Sample treated 2 h at 60° C. | 0.204 |
| Sample treated 2 h at 70° C. | 0.192 |
| Sample treated 2 h at 80° C. | 0.204 |

The thermal hysteresis values thus measured demonstrate the fact that the crystal inhibiting agents contained in the *Zoarces viviparus* serum exhibit a very high heat stability. This is an advantage for the use of such agents in food manufacturing processes involving a high temperature stage, in particular in processes involving a pasteurization stage.

Demonstration of the Influence of the Concentration of *Zoarces viviparus* Serum on the Thermal Hysteresis Value Samples of *Zoarces viviparus* serum are diluted in double-distilled water and the thermal hysteresis value for these samples is measured in the manner described in the test "measurement of thermal hysteresis".

The thermal hysteresis values for these serum samples are stated in Table II below.

TABLE II

| Sample diluted in double-distilled water | Thermal hysteresis value (° C.) |
|---|---|
| Control sample | 0.524 |
| Sample diluted ½ | 0.276 |
| Sample diluted ¼ | 0.164 |
| Sample diluted ⅛ | 0.094 |

The results thus obtained demonstrate the fact that the thermal hysteresis value is dependent on the concentration of the *Zoarces viviparus* serum sample. This dependence is not linear.

Comparative Study of the Activity of Crystal Formation Inhibiting Agents Contained in a Fish Serum The thermal hysteresis is measured for samples of serum extracted from *Gadus morhua*, a fish living on the coasts of Newfoundland, *Pollachius pollachius*, a fish living on the Mediterranean coasts up to the north of Norway, *Gobiuscullus flavescens*, a fish living on the European coasts and on the Japanese coasts, *Myoxocephalus scorpius*, a fish living in the Arctic and near the coasts of Norway, *Liparis liparis*, a fish living on the Atlantic coasts and *Spinachia spinachia*, a fish living in the Bay of Biscay and up to the north of Norway. The thermal hysteresis values for these various samples are compared with the thermal hysteresis value for a sample of *Zoarces viviparus* serum.

All the fish were captured in winter in a Norwegian fjord and were killed at most 3 h before carrying out the thermal hysteresis measurements using serum samples extracted from these fish.

To do this, the procedure is carried out in the manner described in the test "Measurement of thermal hysteresis".

The thermal hysteresis values for these serum samples are stated in Table III below.

TABLE III

| Sample of serum extracted from | Thermal hysteresis value (° C.) |
|---|---|
| *Gadus morhua* | 0 |
| *Pollachius pollachius* | 0 |
| *Gobiuscullus flavescens* | 0.4 |
| *Myoxocephalus scorpius* | 0.1 |
| *Spinachia spinachia* | 0.2 |
| *Liparis liparis* | 0.4 |
| *Zoarces viviparus* | 1.4 |

The thermal hysteresis values thus measured demonstrate the fact that the crystal inhibiting agents contained in the *Zoarces viviparus* serum have an activity greater than those for the crystal inhibiting agents contained in the serum of other fish living under similar conditions.

Measurement of the Size of the Ice Crystals in Ice Cream Containing *Zoarces viviparus* Serum The size of the ice crystals in an ice cream containing *Zoarces viviparus* serum is measured and then these results are compared with the size of ice crystals in an ice cream produced under identical conditions, but not containing *Zoarces viviparus* serum.

To do this, an ice cream containing 0.05% of Zoarces viviparus serum, which was stored at −40° C., is used. 1 cm$^3$ portions are cut out from the middle of the ice cream mass and transferred into a refrigerated chamber at −10° C.

A sample containing 3 mm$^3$ of silicone fat, 3 mm$^3$ of one of the said portions and 7 drops of petroleum benzin is prepared, at −10° C., in a silicone rubber tube. The tube is closed at both ends and its contents are mixed with the aid of a glass rod.

The sample is transferred onto a microscope slide and it is covered with a second microscope slide.

The sample thus prepared is placed under an optical microscope and its image is visualized on a video screen. A binary image representative of the crystals is obtained with the aid of the PC-IMAGE program marketed by Gloor Instrumente A. G., Brauereistrasse 10, CH-8610 Uster. With the aid of the said program, the size of the crystals, expressed in equivalent diameter, is measured.

The size of the ice crystals in a control which is prepared as described above using an ice cream not containing *Zoarces viviparus* serum is measured.

The distribution of the ice crystals in the ice cream containing *Zoarces viviparus* serum is then compared with the control based on the size criterion.

The distribution of the ice crystals in the ice cream containing *Zoarces viviparus* serum (a) and that of the ice crystals in the control (b), based on the size criterion, are indicated in Table IV below.

TABLE IV

| Size of the crystals (μm) | Distribution in (a) | Distribution in (b) |
|---|---|---|
| 0–10 | 1 | 0 |
| 10–20 | 162 | 50 |
| 20–30 | 192 | 132 |
| 30–40 | 116 | 128 |
| 40–50 | 50 | 76 |
| 50–60 | 14 | 27 |
| 60–70 | 12 | 12 |
| 70–80 | 0 | 4 |
| 80–90 | 3 | 0 |
| 90–100 | 0 | 0 |
| 100–110 | 0 | 0 |

From the results stated in Table IV, it can be observed that the small-sized crystals are present in a larger number in the ice cream containing *Zoarces viviparus* serum (a). Indeed, it is possible to demonstrate the fact that, in the ice cream containing *Zoarces viviparus* serum (a), the crystals are predominantly distributed in a size range from 10 to 40 μm, whereas, in the control (b), the crystals are predominantly distributed in the size range from 20 to 50 μm.

Furthermore, from the size values for all the crystals, the mean size of the crystals in the ice cream containing *Zoarces viviparus* serum is calculated and this value is compared with the mean size of the ice crystals in the control. The mean size of the ice crystals in the ice cream containing *Zoarces viviparus* serum is 27.8 μm and that of the ice crystals in the control is 33.8 μm.

Measurement of the size of the ice crystals in the ice cream containing *Zoarces viviparus* serum after a thermal shock The ice cream containing *Zoarces viviparus* serum and the control are subjected to a thermal shock for 36 h. The thermal shock consists in a temperature cycle during which the sample is heated to −4° C. and then cooled to −20° C. and finally heated and cooled in the temperature range of between −4° C. and −20° C.

The procedure is then carried out in the manner described in the test above.

The distribution of the ice crystals in the ice cream containing *Zoarces viviparus* serum is compared, based on the size criterion, with that of the ice crystals in the control.

The distribution of the ice crystals in the ice cream containing *Zoarces viviparus* serum (c) and that of the ice crystals in the control (d), based on the size criterion, are indicated in Table V below.

TABLE V

| Size of the crystals (μm) | Distribution in (c) | Distribution in (d) |
| --- | --- | --- |
| 0–10 | 0 | 0 |
| 10–20 | 1 | 1 |
| 20–30 | 37 | 0 |
| 30–40 | 61 | 2 |
| 40–50 | 61 | 8 |
| 50–60 | 40 | 20 |
| 60–70 | 18 | 25 |
| 70–80 | 14 | 40 |
| 80–90 | 10 | 37 |
| 90–100 | 3 | 41 |
| 100–110 | 6 | 30 |
| 110–120 | 6 | 18 |
| 120–130 | 4 | 18 |
| 130–140 | 1 | 9 |
| 140–150 | 0 | 8 |
| 150–160 | 0 | 6 |
| 160–170 | 0 | 8 |
| 170–180 | 0 | 1 |
| 180–190 | 0 | 3 |
| 190–200 | 0 | 3 |

The results stated in Table V demonstrate the fact that, after a thermal shock, the size of the ice crystals in an ice cream to which *Zoarces viviparus* serum containing crystal growth inhibiting agents is added is smaller than that of the ice crystals in the ice cream to which the said serum has not been added.

Indeed, in the presence of *Zoarces viviparus* serum, the size of 76% of the ice crystals in an ice cream is less than 60 μm, whereas in the control, only 11% of the ice crystals are less than 60 μm in size.

Furthermore, in the presence of *Zoarces viviparus* serum, only 6% of the ice crystals in an ice cream are greater than 100 μm in size, whereas in the control, 38% of the crystals are greater than 100 μm in size.

Finally, from the size values for all the crystals, the mean size of the ice crystals in the ice cream containing *Zoarces viviparus* serum and having undergone a thermal shock is calculated. Next, this value is compared with the mean size of the ice crystals in the control. The mean size of the ice crystals in the ice cream containing *Zoarces viviparus* serum is 50.8 μm and that of the ice crystals in the control is 96.5 μm.

The fact that the recrystallization of the ice crystals is partially inhibited in an ice cream to which *Zoarces viviparus* serum containing crystal growth inhibiting agents has been added and which is then subjected to a thermal shock is therefore demonstrated.

Analysis of the Texture of a Food Product to Which an Extract of *Zoarces viviparus* Serum has been added To analyse the texture of a food product, the energy required to break it is measured with the aid of a texture analyser, in particular Instron Food Testing Instrument marketed by Instron Limited, Coronation Road, High Wycombe, Bucks HP12 3SY, UK.

To do this, the food product is placed on a circular tray, a disc 40 mm in diameter having been scooped out of its centre, and a piston having a circular base 30 mm in diameter is pressed on the top surface of the food product, while measuring the energy required to break it.

The energy required to break thinly sliced cod fillets to which 1 g of *Zoarces viviparus* serum extract containing crystal growth inhibiting agents has been added, and then frozen and cooked, is measured. These measurements are then compared with those carried out on thinly sliced cod fillets without addition of *Zoarces viviparus* serum extract, which were also frozen and then cooked.

COMPARATIVE EXAMPLE 1 g of *Zoarces viviparus* serum extract is therefore mixed in 25 g of water and this solution is added to 1 kg of thinly sliced cod fillets. The whole is well mixed and then divided into 40 g portions. Next, these portions are frozen at −35° C.

By comparison, 25 g of water are mixed with 1 kg of thinly sliced cod fillets which are then divided into 40 g portions, so as to prepare controls. These controls are also frozen at −35° C.

These 40 g portions and the controls are placed in plastic bags and then they are heated to a temperature of 70° C.

Next, the energy required to break the portions and the controls is measured. The measured values are then compared.

The energy required to break thinly sliced cod fillets to which *Zoarces viviparus* serum extract has been added is 10.9±0.3 J/100 g whereas that required to break cod fillets without addition of *Zoarces viviparus* serum extract is 12±0.3 J1100 g.

These results demonstrate the fact that the thinly sliced cod fillets, to which *Zoarces viviparus* serum extract was added and which were frozen, have a more tender texture after cooking than the thinly sliced cod fillets frozen without addition of *Zoarces viviparus* serum extract.

Microscopic Analysis of the Texture of a Solid Food Product

To carry out a microscopic analysis of the texture, a refrigerated microscope is used to evaluate the size of ice crystals present.

To do this, 40 g portions of cod fillets and controls are prepared, in the manner described in the comparative example above, and frozen in a pulsed air freezer at a temperature of −35° C.

Next, samples of these frozen 40 g portions and samples of the frozen controls are observed under a refrigerated microscope so as to evaluate and compare the size of the ice crystals in these various samples.

The fact that the size of the ice crystals contained in thinly sliced cod fillets, to which *Zoarces viviparus* serum extract containing ice crystal growth inhibiting agents has been added and then frozen, is less than that of the ice crystals contained in the thinly sliced cod fillets frozen without addition of *Zoarces vivaparus* serum extract, is demonstrated.

The addition of *Zoarces viviparus* serum extract therefore makes it possible to avoid the damage caused by the increase in the size of ice crystals during freezing, in particular of a solid or fibrous food product.

The following example is presented by way of illustration of one industrial use, in the food sector, of crystal growth inhibiting agents according to the present invention. In the example below, the percentages are given by weight, unless otherwise stated.

Example 1

*Zoarces viviparus* serum containing crystal growth inhibiting agents is used for the manufacture of an ice cream.

To do this, 92.3 g of skimmed milk powder, 150 g of sucrose, 26.2 g of glucose syrup and 5 g of emulsifier are dissolved in 494 g of water at 65° C.

4 g of vanilla flavour and 228.5 g of cream containing 35% fat are added thereto.

This preparation is homogenized in a Rannie type homogenizer marketed by Kindler Maschinen A. G., Postfach 297, CH-8021 Zurich, in two successive runs, the first at 140 bar and the second at 40 bar.

The homogenized preparation is pasteurized at 83° C. for 30 s in a plate exchanger.

It is cooled to 4° C. and allowed to stand for 12 h at this temperature before adding 0.05% of *Zoarces viviparus* serum and carrying out the freezing in a HOYER MF50 type freezer marketed by APV TECHNOHOY, Axel Kiers Vej 28–30, DK-8270 Aarhus-Hojbjerg.

An ice cream having a foamy texture is thus obtained.

This ice cream is then hardened in a pulsed air cooling cell and it is stored at −35° C.

After tempering at −18° C., this ice cream has a smooth and unctuous texture.

What is claimed is:

1. An ice crystal growth inhibiting agent comprising a purified protein fraction of thermal hysteresis proteins obtained from *Zoarces viviparus*, said protein fraction having a molecular weight of 4 to 5.5 kDa and a thermal hysteresis of 1 to 1.8° C.

2. The ice crystal growth inhibiting agent according to claim 1, wherein said protein fraction is obtained by a process comprising:
   (i) collecting serum containing thermal hysteresis proteins from *Zoarces viviparus*;
   (ii) isolating said thermal hysteresis proteins from said serum; and
   (iii) separating said protein fraction from said thermal hysteresis proteins by gel filtration.

3. The ice crystal growth inhibiting agent according to claim 1, wherein said protein fraction has a thermal hysteresis of 1.3 to 1.5° C.

4. A food product comprising an ice crystal growth inhibiting agent according to claim 1.

5. The food product according to claim 4, wherein said food product is a frozen food product.

6. The food product according to claim 5, wherein said food product includes ice crystals in a size range predominantly from 10 μm to 60 μm.

7. The food product according to claim 6, wherein said frozen food product is ice cream and at least 76% of said ice crystals are in said size range.

8. A process for preparing an ice crystal inhibiting agent which comprises obtaining a protein fraction of thermal hysteresis proteins, said protein fraction having a molecular weight of 4 to 5.5 kDa and a thermal hysteresis of 1 to 1.8° C., said protein fraction prepared by extracting said fraction from *Zoarces viviparus* serum, said serum prepared by:
   (i) extracting blood from a source of *Zoarces viviparus*;
   (ii) cooling said blood at a temperature sufficient to allow for the formation of a supernatant portion containing said serum;
   (iii) collecting said ice growth inhibiting agent containing serum from said supernatant; and
   (iv) utilizing said fraction as said ice crystal inhibiting agent.

9. The process according to claim 8, wherein said protein fraction has a thermal hysteresis of 1.3° C. to 1.5° C.

10. The process according to claim 8, wherein said blood is extracted by using a treated capillary.

11. The process according to claim 8, wherein said ice crystal growth inhibiting agent is obtained by fractionation of said supernatant.

12. The process according to claim 8, further comprising freezing said supernatant.

13. The process according to claim 8, further comprising adding said ice crystal inhibiting agent to a food product.

14. The process according to claim 13, further comprising said food product and said ice crystal inhibiting agent to obtain ice crystals therein, said food product having at least 76% of the ice crystals in a size range of from 10 μm to 60 μm.

15. The process according to claim 14, wherein said food product is ice cream.

16. A process for reducing the size of ice crystals of a food product comprising adding an ice crystal growth inhibiting agent of claim 1 to a food product in an amount sufficient to obtain reduced size ice crystals therein when the food product is frozen.

17. The process according to claim 16, wherein said ice crystal growth inhibiting agent is present in an amount of from 0.01 to 10% by volume of said food product.

18. The process according to claim 16, further comprising freezing said food product and a sufficient amount of the ice crystal growth inhibiting agent to obtain ice crystals predominantly in a size range of from 10 μm to 60 μm.

19. The process according to claim 18, wherein said food product is frozen at a temperature from −15° C. to −40° C.

20. The process according to claim 18, wherein said food product is an ice cream.

* * * * *